(12) United States Patent
Leal (10) Patent No.: US 10,299,503 B2
(45) Date of Patent: May 28, 2019

(54) N-ACETYL CYSTEINE BASED COMPOSITIONS

(71) Applicant: Jesus Leal, Denville, NJ (US)

(72) Inventor: Jesus Leal, Denville, NJ (US)

(73) Assignee: Recommended by Mom LLC, Denville, NJ (US)

( * ) Notice: Subject to any disclaimer, the term of this patent is extended or adjusted under 35 U.S.C. 154(b) by 0 days.

(21) Appl. No.: 15/877,570

(22) Filed: Jan. 23, 2018

(65) Prior Publication Data

US 2018/0206545 A1    Jul. 26, 2018

Related U.S. Application Data (60) Provisional application No. 62/449,833, filed on Jan. 24, 2017.

(51) Int. Cl.
    *A23L 33/00*    (2016.01)
    *A23L 33/15*    (2016.01)
    (Continued)

(52) U.S. Cl.
    CPC .............. *A23L 33/40* (2016.08); *A23L 5/44* (2016.08); *A23L 23/00* (2016.08); *A23L 33/10* (2016.08);
    (Continued)

(58) Field of Classification Search
    CPC .......... A23L 33/40; A23L 23/00; A23L 33/15; A61P 43/00
    See application file for complete search history.

(56) References Cited

U.S. PATENT DOCUMENTS 6,846,494 B1 *   1/2005   Verheul-Koot ....... A23L 33/175
                                                          424/439
2014/0034523 A1  2/2014   Valentine
                          (Continued)

FOREIGN PATENT DOCUMENTS

EP    0848951       *   6/1998
EP    0848951 A1    *   6/1998
                          (Continued)

OTHER PUBLICATIONS

Notification of Transmittal of the International Search Report and Written Opinion of the International Searching Authority for Application No. PCT/US2018/14804 dated Mar. 29, 2018, 10 pgs.
(Continued)

*Primary Examiner* — Carlos A Azpuru
(74) *Attorney, Agent, or Firm* — Lowenstein Sandler LLP (57) ABSTRACT

A composition for improving the health of a subject in a manner comparable to a bowl of homemade chicken soup is provided. The composition may include n-acetyl cysteine, vitamin C, and one or more carotenoids. The composition may be designed for oral consumption in a variety of dosage forms. The composition may be delivered utilizing a portable all-in-one delivery system. The delivery system may include an interconnected two piece bottle cap that together define a storage chamber that may hold the composition, and a bottle with a solvent connected to the interconnected two-piece bottle cap. The interconnected two-piece bottle cap may be in a locked or in an open state. The composition may be released into the solvent when the two-piece bottle cap interconnection is in the open state. The two-piece bottle cap may further include a delivery mechanism that switches the two-piece bottle cap interconnection from the closed state to the open state.

13 Claims, 1 Drawing Sheet

(51) Int. Cl.
  *A23L 5/44* (2016.01)
  *B65D 51/28* (2006.01)
  *B65D 41/04* (2006.01)
  *A61K 9/00* (2006.01)
  *A61P 43/00* (2006.01)
  *A61K 31/10* (2006.01)
  *A23L 33/10* (2016.01)
  *A23L 33/155* (2016.01)
  *A23L 33/175* (2016.01)
  *A23L 23/00* (2016.01)

(52) U.S. Cl.
  CPC .............. *A23L 33/15* (2016.08); *A23L 33/155* (2016.08); *A23L 33/175* (2016.08); *A61K 9/0095* (2013.01); *A61K 31/10* (2013.01); *A61P 43/00* (2018.01); *B65D 41/04* (2013.01); *B65D 51/2864* (2013.01); *A23V 2002/00* (2013.01); *A23V 2250/0634* (2013.01); *A23V 2250/211* (2013.01); *A23V 2250/708* (2013.01)

(56) References Cited

U.S. PATENT DOCUMENTS

2014/0265760 A1  9/2014  Layne et al.
2015/0196577 A1  7/2015  Rinsch et al.

FOREIGN PATENT DOCUMENTS

WO  2016088116  *  6/2016
WO  2016088116 A1  *  6/2016

OTHER PUBLICATIONS

Li, et al, "Synergistic Protection of N-Acetylcysteine and Ascorbic Acid 2-Phosphate on Human Mesenchymal Stem Cells Against Mitoptosis, Necroptosis and Apoptosis", Scientific Reports 5, Article No. 8919, Apr. 24, 2015, 37 pages.

* cited by examiner

N-ACETYL CYSTEINE BASED COMPOSITIONS

FIELD OF THE INVENTION

The present invention relates generally to ingestible compositions, and in particular to compositions containing n-acetyl cysteine (NAC). Particularly, the present invention relates to a formulation comprising NAC, vitamin C and optionally other antioxidants found in homemade chicken soup.

BACKGROUND OF THE INVENTION

Chicken soup is a common remedy to temporarily relieve symptoms associated with the common cold. Since the days of the early Egyptians, homemade chicken soup has been widely accepted as an aid for treating symptoms of the common cold. However, the cumbersome task of cooking homemade chicken soup has become an impediment for patients to consume it when needed. In recent history, researchers have tried, and ultimately failed, to identify exactly why chicken soup provides these temporary health benefits. Part of the problem is that there are countless recipes for chicken soup, and each recipe varies in the number and combination of ingredients that supply nutrients such as proteins, fats, vitamins and minerals. Therefore, identifying a particularly advantageous formulation becomes a challenging task.

To solve these problems, several attempts have been made to dehydrate, reduce, or otherwise condense chicken soup to a cube or "pill" for consumption. While this strategy ensures that the key components of chicken soup are present in the resulting cube or "pill" (without the water), these products tend to be too large for swallowing, or require hydration back to a soup-like form. Products that require hydration to a soup-like form have an added hurdle because they are not portable and/or require an individual to utilize a number of containers when preparing the product for consumption. Additionally, the products described do not provide the opportunity to increase the amounts of particular ingredients while keeping a dosage form that remains easy to swallow.

Therefore, a need exists to provide a formulation of particular components of chicken soup, formulated in a dosage form sized and flavored for ease of oral ingestion and for ease of preparation.

SUMMARY OF THE INVENTION

In some embodiments, the present invention relates to a composition that includes particular ingredients found in chicken soup that are believed to improve the health of a subject. The composition includes NAC. The composition may further include vitamin C, carotenoids (such as Beta Carotene, Alpha Carotene, Lutein, Vitamin A, and Zeaxanthin) and other vitamins and minerals. The composition may be designed for oral consumption in a solid dosage form such as tablets, capsules, dispersible powders or granules, or a liquid dosage form such as solutions or suspensions. In certain embodiments, none of the components found in the composition are produced or derived from the extraction, dehydration or other manipulation of chicken soup.

In some embodiments, the present invention relates to an all-in one delivery system. The delivery system may comprise a two-piece bottle cap comprising two pieces. The two pieces may define a storage chamber. The storage chamber may comprise the compositions disclosed herein. The delivery system may further comprise a bottle with a solvent. The two pieces in the two-piece bottle cap may be interconnected in a plurality of states (e.g., in an open state or in a closed state). When the two pieces are interconnected in an open state, the composition held in the storage chamber may be released into the solvent in the bottle. When the two pieces are interconnected in a closed state, the composition held in the storage chamber may be maintained in the storage chamber without being released. The two-piece bottle cap may comprise a composition delivery mechanism (e.g., a push activation mechanism or a twist activation mechanism) that may switch the interconnection between the two pieces in the two-piece bottle cap from one state to another (e.g., from the closed state to the open state).

In some embodiments, the present invention relates to a method of treating a disease or condition by administering the composition disclosed herein to a patient in need thereof.

BRIEF DESCRIPTION OF THE DRAWINGS

The above and other features of the present disclosure, their nature, and various advantages will become more apparent upon consideration of the following detailed description, taken in conjunction with the accompanying drawings, in which.

DETAILED DESCRIPTION

It is to be understood that the descriptions of the present invention have been simplified to illustrate elements that are relevant for a clear understanding of the present invention, while eliminating, for the purpose of clarity, many other elements found in typical ingestible compositions. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

In some embodiments, the present invention provides amounts of immune boosting ingredients found in chicken soup in a flavored drink, e.g. an orange, fruit punch, cherry, creamy vanilla, mango, or tangerine flavored effervescent drink. In some embodiments, the formulations disclosed herein have various advantages, including but not limited to, unique portability of homemade chicken soup by removing the need to refrigerate, heat, or cook the soup (the formula may be placed in children's lunch boxes as a drink, in briefcases, purses etc); a flavored drink with the antioxidant components found in chicken soup; an alternative to patients who should not or cannot take antihistamine or decongestants without consulting their physician because of their medical condition (e.g., hypertension, heart disease, prostate enlargement, glaucoma, chronic obstructive pulmonary disease (COPD), asthma, gout, etc); a phosphorus free, chicken soup formula for patients suffering from hyperphosphatemia; a substantially manganese free (e.g., reduced from 15 mg of manganese to about 0.67 mg/dose for a daily requirement of about 2 mg) chicken soup formula for patients with liver disease; a sodium reduced chicken soup formula for patients on sodium restricted diets; improving the immunological benefits of canned soups; safety for patients that seek to ingest individual supplements of antioxidants that are available only in mega-doses; provides benefits of chicken soup to individuals who do not like the flavor of chicken soup; and combinations thereof.

The present invention includes a series of formulations for treating at least some of the symptoms associated with the common cold and mucosal clearance. In one embodiment, compositions disclosed herein may be administered to boost the immune system of a patient in need thereof. In another embodiment, composition disclosed herein may be administered to thin the mucus of a patient in need thereof. For example, without being bound to any particular theory, it is believed that compositions containing NAC may break up mucoproteins in lung mucus by cleaving disulfide bonds and converting them into sulfhydryl groups. This may result in the reduction of the mucoprotein chain lengths, thereby thinning the mucus. Such activity may improve symptoms for conditions such as bronchitis and flu. By further example, compositions NAC and/or the carotenoids may also help prevent influenza by stimulation of the immune system. The present invention may further be helpful for individuals with chronic bronchitis by reducing frequency of acute flare-ups. Another beneficial effect is an attenuation of the inflammatory response and the inhibition of neutrophil chemotaxis. The present invention may be suitable for use by any living animal, such as mammals, and most preferably humans.

According to an embodiment of the present invention, an exemplary formulation may comprise NAC. According to certain embodiments of the present invention, an exemplary formulation may comprise NAC and vitamin C. In certain embodiments, an exemplary formulation may further comprise one or more other ingredients, such as carotenoids. The carotenoids may be selected from the group consisting of beta carotene, alpha carotene, lutein, and zeaxanthin. In certain exemplary formulations, additional bioflavonoids, vitamins, minerals, pharmaceutically acceptable excipients (e.g., bitterness suppressors, flavoring agents, amino-acid maskers) and combinations thereof may be included as additional ingredients.

The composition may be designed for oral consumption in a solid dosage form, such as tablets, sachets, capsules or dispersible powders or granules. In some embodiments, the composition may be in a form of a chewable tablet. The composition may alternatively be designed in a liquid dosage form, such as syrups, emulsions, solutions or suspensions. Such dosage forms may be sized for ease of oral ingestion and preferably formulated in a single unit, though multiple unit dosages may also be used. Any of the compositions disclosed herein may further comprise an effervescent. In some embodiments, the compositions disclosed herein may be free of an effervescent. For instance, in one embodiment, the composition may be in a form of a powder or granules and comprise an effervescent. In another embodiment, the composition may be in a form of a powder or granules and not comprise an effervescent. Descriptions of the ingredients contained in the formulations of the present invention are provided in the following paragraphs.

NAC is the ingredient in chicken soup that helps relieve symptoms of the common cold. It is also a metabolite of the sulfur-containing amino acid, Cysteine. NAC is rapidly metabolizes to intracellular glutathione, which acts as an antioxidant in the body. Glutathione also detoxifies chemicals into less harmful compounds, aids in the transport of nutrients to lymphocytes and phagocytes, and protects cell membranes. While purified glutathione is available as a dietary supplement, NAC is thought to be a better method of boosting cellular glutathione levels.

NAC can cleave disulfide bonds by converting them to two sulfhydryl groups, which result in the breakup of mucoproteins in mucus. NAC may also protect lung tissue through anti-oxidant activity. NAC has also been shown to reduce the proliferation of certain cells lining in the colon and may reduce the risk of colon cancer in people with recurrent polyps in the colon. Its action as an antioxidant and a glutathione precursor may also contribute to a protective effect against cancer. NAC at a dosage of 1,200 mg per day may help to prevent influenza and reduce symptoms and duration of existing influenza infection.

Typical daily dosage recommendations of NAC may fall within the range of 250-1500 mg for the majority of therapeutic benefits, and may be taken once a day or in divided doses (such as twice or three-times daily). The compositions disclosed herein comprise NAC in an amount of about 100-1500 mg, about 150-1200 mg, about 100-200 mg, about 400-1000 mg, about 500-800 mg, or about 550-650 mg.

Since NAC contains sulfur, it may impart an unpleasant smell and/or taste if it is not encapsulated or if it is simply dissolved or suspended in water. In some embodiments, the composition disclosed herein comprises a combination of amino acid masking agents and NAC. The amino acid masking agents may contribute to the pleasant taste and smell of the NAC composition. The compositions disclosed herein may comprise an amino acid masking agent in an amount of about 1-250 mg, about 10-100 mg, about 25-75 mg, or about 30-50 mg. In some embodiments, the composition comprises about 0.1-5 wt %, about 0.3-3 wt %, or about 0.5-1.2 wt % of amino acid masking agent(s) based on the total weight of the composition.

In some embodiments, the compositions discussed herein may further comprise vitamin C. Vitamin C is a water-soluble vitamin necessary for normal growth and development, as it is required for the growth and repair of body tissues. For example, it is necessary to form collagen and cartilage (an important protein used to make skin, scar tissue, tendons, ligaments, and blood vessels). Vitamin C is also an antioxidant that slows down damage caused by free radicals. Antioxidants remove destructive free radicals from the body before they cause tissue damage that can lead to chronic diseases like heart disease and cancer. Vitamin C may be added to the formulation in some embodiments to boost the efficacy of the ingredients found naturally in chicken soup. Vitamin C may be present in the compositions disclosed herein as ascorbic acid. The compositions disclosed herein may comprise vitamin C in an amount of about 1-1500 mg, about 200-1000 mg, about 900-1100 mg, about 300-350 mg, about 300-400 mg, about 300-500 mg, or about 400-600 mg.

In some embodiments, the compositions discussed herein may further comprise beta carotene. Beta carotene is a carotenoid, which is a highly pigmented, fat-soluble compound. It can be converted to vitamin A, and therefore it is considered a provitamin Beta carotene also possesses antioxidant properties. Further, beta-carotene is converted to retinol (vitamin A), which is essential for vision and is subsequently converted to retinoic acid, which is used for processes involving growth and cell differentiation. Adults and teenagers may need 6 to 50 mg of beta-carotene (the equivalent of 10,000 to 83,000 IU of vitamin A activity) per day. In certain embodiments of the present invention, vitamin A can also be directly used, either in addition to or as a replacement to a vitamin A precursor. The compositions disclosed herein may comprise beta carotene in an amount of about 0.5-10 mg, about 1.5-5 mg, about 0.5-0.8 mg, or about 2-3 mg.

In some embodiments, the compositions discussed herein may further comprise alpha-carotene. Alpha-carotene is also part of the carotenoid family. Like beta-carotene, alpha-carotene is converted into vitamin A for the maintenance of healthy skin and bones, good vision, and a robust immune system. As a precursor to vitamin A, alpha-carotene is only about half as effective as beta-carotene. However, alpha-carotene may be even more effective than beta-carotene in its role as an antioxidant. In addition, alpha-carotene may help prevent cancer by stimulating cell-to-cell communication, a process necessary to ensure proper cell division. In some embodiments of the present invention, the ratio of beta-carotene to alpha-carotene in the compositions or formulations disclosed herein may be similar to the ratio of beta-carotene to alpha-carotene typically found in chicken soup. The compositions disclosed herein may comprise alpha-carotene in an amount of about 32-32,000 mcg, about 100-10,000 mcg, about 200-5,000 mcg, about 100-150 mcg, about 100-500 mcg, about 300-1,000 mcg, or about 400-600 mcg.

In some embodiments, the compositions discussed herein may further comprise calcium. Calcium is one of the most important minerals for the growth, maintenance, and reproduction of the human body. Calcium is best known for its role in the development and maintenance of healthy bones and teeth, where the majority of calcium is stored. Calcium can also be found in the blood, and is critical for proper muscle contraction, blood pressure regulation, and nerve function. Calcium further helps with blood clotting, nerve signaling, muscle contraction and relaxation, and the release of certain hormones. It is also needed for a normal heartbeat. The compositions disclosed herein may comprise calcium as a granular calcium carbonate. The compositions disclosed herein may comprise calcium in an amount of about 2-200 mg, about 5-100 mg, about 5-10 mg, about 5-30 mg, about 10-50 mg, or about 20-35 mg.

In some embodiments, the compositions discussed herein may further comprise thiamine. Thiamine is one of the B vitamins (vitamin B1), a group of water-soluble vitamins that participate in many of the chemical reactions in the body. Thiamine helps the body cells convert carbohydrates into energy. It is also essential for the functioning of the heart, muscles, and nervous system. It is often referred to as an "anti-stress" vitamin. The compositions disclosed herein may comprise thiamine as a powder thiamine mononitrate (vitamin B1). The compositions disclosed herein may comprise thiamine in an amount of about 60-6,000 mcg, about 200-300 mcg, about 200-250 mcg, about 500-3,000 mcg, about 700-1,500 mcg, about 200-950 mcg, or about 800-1,000 mcg.

In some embodiments, the compositions discussed herein may further comprise magnesium. Magnesium is one of the most important minerals and helps activate a variety of enzyme systems in the body. Magnesium is vital for energy production and carbohydrate metabolism. It also influences calcium metabolism and is involved in bone health and muscle function. Magnesium serves several important metabolic functions, such as in the production and transport of energy. It is also important for the contraction and relaxation of muscles. Magnesium is involved in the synthesis of protein. The compositions disclosed herein may comprise magnesium as granular magnesium oxide. The compositions disclosed herein may comprise magnesium in an amount of about 2-200 mg, about 5-10 mg, about 5-30 mg, about 10-100 mg, about 15-50 mg, or about 20-35 mg.

In some embodiments, the compositions discussed herein may further comprise zinc. Zinc is necessary for the functioning of more than three hundred different enzymes, and plays a vital role in an enormous number of biological processes. For example, zinc is needed for muscle growth, insulin function, vision, and taste perception, and is second only to iron in its concentration in the body. It is also required for proper immune system function, and may be used as an immune system booster. Zinc supports prostate health and the body's ability to protect itself against heavy metal toxicity, such as cadmium and lead. It plays a role in cell division, cell growth, wound healing, and the break down of carbohydrates. The compositions disclosed herein may comprise zinc as zinc sulfate. The compositions disclosed herein may comprise zinc in an amount of about 44-4,400 mcg, about 100-2,000 mcg, about 300-1,000 mcg, about 150-700 mcg, about 150-200 mcg, or about 500-800 mcg.

In some embodiments, the compositions discussed herein may further comprise lutein. Lutein is a xanthophyll and is a member of the carotenoid family, along with beta-carotene and alpha-carotene. However, unlike alpha- and beta-carotene, lutein is not converted by the body to vitamin A. Like other carotenoids, lutein is an antioxidant. Lutein helps protect the eyes and skin from ultraviolet (UV) damage by blocking blue (UV) light from absorption, and may also lower the risk of developing age-related macular degeneration, as well as reversing symptoms of macular degeneration. The compositions disclosed herein may comprise lutein in an amount of about 4-400 mcg, about 10-55 mcg, about 10-15 mcg, about 20-200 mcg, about 30-100 mcg, or about 40-60 mcg.

In some embodiments, the compositions discussed herein may further comprise zeaxanthin. Zeaxanthin is also a xanthophyll, and is therefore also part of the carotenoid family. It provides the body with anti-inflammatory and antioxidant protection. Like lutein, zeaxanthin helps protect the eye from ultra-violet (UV) damage, and prevents free-radical damage to the retina and the lens of the eye that is associated with diabetic retinopathy, macular degeneration, cataracts, and glaucoma. The compositions disclosed herein may comprise zeaxanthin in the form of a powder. The compositions disclosed herein may comprise zeaxanthin in an amount of about 0.5-50 mcg, about 1.5-8 mcg, about 1.5-2 mcg, about 2-30 mcg, about 4-15 mcg, or about 5-8 mcg.

In some embodiments, the compositions discussed herein may further comprise additional pharmaceutically acceptable excipients. Pharmaceutically acceptable excipients may include, without limitations, dextrose, ascorbic acid, sucralose, citric acid, malic acid, bitterness suppressors, ethyl maltol, salt, vegetable fibers, magnesium stearate, sodium bicarbonate, flavoring agents (e.g., fruit punch, cherry, creamy vanilla, orange, mango, tangerine flavor, or combinations thereof), trace amounts of manganese, trace amounts of phosphorus and combinations thereof. The total amount of pharmaceutically acceptable excipients in the composition may be about 0.1-95 wt %, about 50-92 wt %, about 90-95 wt %, or about 75-90 wt %.

Pediatric compositions in accordance with embodiments disclosed herein may comprise about 590-610 mg of a proprietary blend of NAC and one or more antioxidants, about 7,500-8,500 IU of vitamin A (as alpha-carotene and beta carotene), about 0.5-1 mg of vitamin B1 (as thiamine mononitrate), about 300-500 mg of vitamin C (as ascorbic acid), about 15-20 mg of magnesium (as magnesium oxide), about 0.1-0.3 mg of zinc (as zinc oxide), and about 10-30 mg sodium.

Adult compositions in accordance with embodiments disclosed herein may comprise about 590-610 mg of a proprietary blend of NAC and one or more antioxidants, about 7,500-8,500 IU of vitamin A (as alpha-carotene and beta carotene), about 0.5-1 mg of vitamin B1 (as thiamine mononitrate), about 900-1100 mg of vitamin C (as ascorbic acid), about 15-20 mg of magnesium (as magnesium oxide), about 0.1-0.3 mg of zinc (as zinc oxide), and about 10-30 mg sodium.

In certain embodiments, the compositions disclosed herein consist essentially of NAC and a carotenoid selected from the group consisting of alpha-carotene, beta-carotene, lutein, zeaxanthin and combinations thereof.

In certain embodiments, the compositions disclosed herein consist essentially of NAC, vitamin C, and a carotenoid selected from the group consisting of alpha-carotene, beta-carotene, lutein, zeaxanthin and combinations thereof.

In certain embodiments, the compositions disclosed herein consist essentially of NAC, vitamin C, a carotenoid selected from the group consisting of alpha-carotene, beta-carotene, lutein, zeaxanthin and combinations thereof, and a pharmaceutically acceptable excipient as disclosed herein.

In certain embodiments, the compositions disclosed herein consist essentially of NAC, vitamin C, and pharmaceutically acceptable excipient as disclosed herein.

In certain embodiments, the compositions disclosed herein consist essentially of NAC, a carotenoid selected from the group consisting of alpha-carotene, beta-carotene, lutein, zeaxanthin and combinations thereof, and a pharmaceutically acceptable excipient as disclosed herein.

In certain embodiments, the components of the compositions disclosed herein (e.g., NAC, vitamin C, various carotenoids, and various pharmaceutically acceptable excipients) are not derived from chicken soup (e.g., by dehydrating chicken soup).

According to an embodiment of the present invention, one or more of the preceding ingredients making up the various formulations may be provided in range of dosages. The various formulations encompassed by embodiments of the present invention may be in a solid dosage form, such as tablets, capsules or dispersible dry powders or granules or in a liquid dosage form, such as syrups, emulsions, solutions or suspensions. The formulations may comprise water in some embodiments (for instance the composition may be formulates as a dry powder or granule that is suspended in an aqueous solvent). In other embodiments, the formulations may be combined with water prior to consumption by the patient. The amount of water used with the formulation may vary depending on the patient's needs and/or restrictions. For instance, a younger child or a water restricted patient may only be allowed to consume smaller amounts of fluid and by combining the formulation with a smaller amount of water, could still benefit from the formulation and from ingredients found in chicken soup. In some embodiments, the powder or granules of the present invention may be separately co-packaged with a suitable amount of water (e.g., in a delivery system as described in detail below). For example, a powder or granule envelop can be adhered to a standard water bottle or the powder or granules can be placed into the cap of a water bottle forming an all-in-one delivery system.

Figures 1, 2, 3:
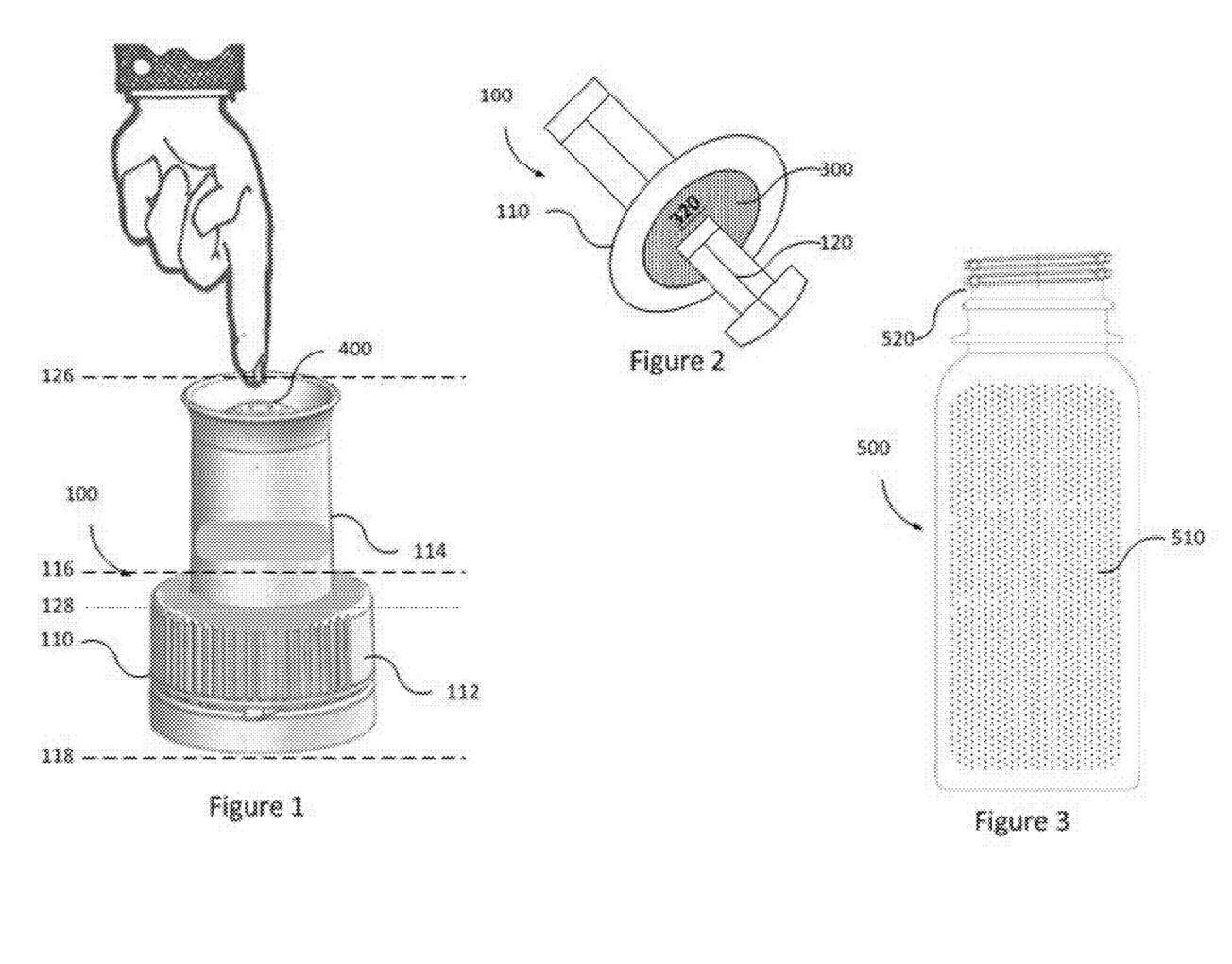
FIG. 1 depicts an exemplary activation mechanism of a two-piece bottle cap according to embodiments.
FIG. 2 depicts a lower prospective view of a two-piece bottle cap according to embodiments.
FIG. 3 depicts a side view of a bottle according to embodiments.

According to certain embodiments, the present invention may be directed to an all-in-one delivery system. The delivery system may comprise a two-piece bottle cap. An exemplary two-piece bottle cap is depicted in FIGS. 1 through 3. The two-piece bottle cap will be described in accordance with the Figures. However, it should be understood by one of ordinary skill in the art that the Figures are merely illustrative and should not be construed as limiting. The two piece bottle cap 100 may comprise two pieces. One piece, also referred to herein as the outer piece 110, may have two parts, a bottom part 112 and a top part 114. The bottom part 112 may have the form of a round bottle cap having a first diameter and a first height. The top part 114 may have the form of an elongated tube having a second diameter and a second height. The first diameter of the bottom part 112 may be bigger than the second diameter of the top part 114. For instance, the first diameter may be about 75% bigger, about 50% bigger, about 45% bigger, about 40% bigger, about 35% bigger, about 30% bigger, or about 25% bigger than the second diameter. The second height of the top part 114 may be longer than the first height of the bottom part 112. For instance, the second height may be about 5 times, about 4.5 times, about 4 times, about 3.5 times, about 3 times, about 2.5 times, or about 2 times bigger than the first height.

Bottom part 112 may comprise a proximal end 116 and a distal end 118, the distal end being closer to a bottle 500 and the proximal end being positioned opposite to the distal end. Top part 114 may also comprise a proximal end 126 and a distal end 128. The proximal end 116 of bottom part 112 may be integral to the distal end 128 of top part 114.

The second piece may also be referred to herein as inner piece 120. Inner piece 120 may have the shape of a piston. Inner piece 120 may be connected to outer piece 110. The two pieces may together define a storage chamber 300. The storage chamber may comprise any of the compositions disclosed herein.

In some embodiments, delivery system may further comprise a bottle 500 and the two-piece bottle cap 100 may be connected to the bottle 500 (e.g., twisted onto a bottle through protrusions 520 compatible to receive the bottom part 112). The bottle may comprise a solvent 510. The solvent may be an aqueous solvent (e.g., water).

The two pieces in the two-piece bottle cap may be interconnected in a plurality of states. The plurality of states may include, without limitations, an open state and a closed state. When the two pieces of the two-piece bottle cap are interconnected in the open state, the composition held in the storage chamber 300 may be released. If the two-piece bottle cap is twisted onto a bottle and the interconnection is in the open state, the composition held in the storage chamber may be infused into the solvent 510. When the two pieces of the two-piece bottle cap are interconnected in the closed state, the composition held in the storage chamber may remain in the storage chamber 300 unreleased. FIG. 3 depicts an illustrative open state where inner piece 120 is pushed down such that it does not block storage chamber 310. When the two-piece bottle cap is in a closed position, inner piece 120 may block storage chamber 310.

In some embodiments, the two-piece bottle cap may further comprise a composition delivery mechanism that may switch the interconnection between the two pieces from one state to another (e.g., from a closed state to an open state). In some embodiments, the composition delivery mechanism may be push activated mechanism (e.g., as shown in FIG. 4) or a twist activated mechanism. In a push activated mechanism, the top part 114 may include a dome shape 400 on its proximal end 126. Pushing the two piece bottle-cap in a certain location (e.g., in the dome shape 400) may switch the interconnection from the closed state to the open state (e.g., by pushing inner piece 120 down and un-blocking storage chamber 300), thereby releasing the composition 320 from the storage chamber into the solvent. In a twist activated mechanism, twisting the two piece bottle cap in a certain manner may switch the interconnection from the closed state to the open state, thereby releasing the composition from the storage chamber into the solvent.

In some embodiments, the amount of solvent in the bottle may be limited by the amount permitted in an airplane cabin (e.g., about 3.0-3.4 oz).

In some embodiments, the present disclosure may be directed to a method of treating a disease or a condition as disclosed herein. The method may comprise administering to a patient in need thereof a composition according to any of the embodiments discussed herein. Exemplary disease or conditions that may be treated include, without limitations, influenza, chronic bronchitis, inflammatory response, neutrophil chemotaxis, various cancers (e.g., colon cancer), common cold, etc. The present disclosure may be directed to a method of boosting an immune system of a patient in need thereof. The present disclosure may be directed to a method of thinning mucus.

In some embodiments, the method of treatment may comprise adding any of the compositions disclosed herein to consumable food or beverages prior to consumption by a patient in need thereof. In some embodiments, the method of treatment may comprise administering any of the compositions disclosed herein before, during, or after a cold. In some embodiments, the method of treatment may comprise administering once daily, twice daily, three times daily, four times daily, five times daily, or six times daily any of the compositions disclosed herein to a patient in need thereof. In one embodiment, the method of treatment may comprise administering once in the morning and once in the evening any of the compositions disclosed herein to a patient in need thereof.

In some embodiments, compositions disclosed herein may be one or more: kosher certified, halal certified, vegan, gluten free, suitable for individual diagnosed with celiac disease, etc.

ILLUSTRATIVE EXAMPLES

The following examples are set forth to assist in understanding the embodiments described herein and should not be construed as specifically limiting the embodiments described and claimed herein. Such variations, including the substitution of all equivalents now known or later developed, which would be within the purview of those skilled in the art, and changes in formulation or minor changes in experimental design, are to be considered to fall within the scope of the embodiments incorporated herein.

Example 1

A first exemplary formulation includes an amount of each ingredient within a predetermined range so as to provide the body with multiple health benefits. Amounts in Table 1 may be provided in a solid dosage form of less than two units, such as two tablets, capsules, or the equivalent in dispersible powder/granules, or up to about 100 ml of liquid dosage forms, such as a solution or suspension. As will be appreciated by those of ordinary skill in the art, "IU" refers to "international units", "mg" refers to "milligrams", and "mcg" refers to "micrograms".

TABLE 1

| Ingredient | Amount Per Serving |
| --- | --- |
| Beta Carotene | 500-83,000 IU |
| Alpha Carotene | 32-32,000 mcg |
| N-acetyl cysteine | 250-1500 mg |
| Lutein | 4-400 mcg |
| Zeaxanthin | 0.5-50 mg |

Example 2

A second exemplary formulation includes an amount of each ingredient within a predetermined range so as to provide the body with multiple health benefits. Amounts in Table 2 may be provided in a solid dosage form of less than two units, such as two tablets, capsules, or the equivalent in dispersible powder/granules, or up to 100 ml of liquid dosage forms, such as a solution or suspension.

TABLE 2

| Ingredient | Amount Per Serving |
| --- | --- |
| Vitamin C | 1-1500 mg |
| Beta Carotene | 500-83,000 IU |
| Alpha Carotene | 32-32,000 mcg |
| Calcium | 2-200 mg |
| Thiamine | 60-6000 mcg |
| Magnesium | 2-200 mg |
| Manganese | 0.6-60 mg |
| Phosphorous | 12-1,200 mg |
| Zinc | 44-4,400 mcg |
| N-acetyl cysteine | 250-1500 mg |
| Lutein | 4-400 mcg |
| Zeaxanthin | 0.5-50 mg |

Example 3

According to an embodiment of the present invention, and as is shown in Table 3, a third exemplary formulation provides a preferred dosage of each ingredient to provide the body with multiple health benefits. Dosage amounts in Table 3 may be provided in a solid dosage form of less than two units, such as two tablets, capsules, or the equivalent in dispersible powder/granules, or up to 100 ml of liquid dosage forms, such as a solution or suspension.

TABLE 3

| Ingredient | Amount Per Serving |
| --- | --- |
| Vitamin C | 500 mg child or 1000 mg adult |
| Beta Carotene | 8076 IU |
| Alpha Carotene | 473 mcg |
| Calcium | 28 mg |
| Thiamine | 900 mcg |
| Magnesium | 28 mg |
| Zinc | 668 mcg |
| N-acetyl cysteine | 600 mg |
| Lutein | 53 mcg |
| Zeaxanthin | 6.5 mcg |

Example 4: Daily Dose Ranges Found in Chicken Soup

Table 4 summarizes the daily dosage range of the ingredients found in a typical 12 ounce serving of chicken soup.

TABLE 4

| Ingredient | Daily Dose Range |
| --- | --- |
| Beta Carotene | 500-500,000 IU (or 3-3000 mg) |
| Alpha Carotene | 32-32,000 mcg |
| N-acetyl cysteine | 250-4500 mg |
| Lutein | 0.4-10000 mcg |
| Zeaxanthin | 0.4-10000 mcg |
| Zinc | 2-18000 mcg |
| Manganese | 600-30000 mcg |
| Magnesium | 2-600 mg |
| Thiamine | 0.1-100 mg |
| Calcium | 2-1200 mg |
| Vitamin C | 250-4500 mg |

Example 5

Table 5 illustrates a fourth exemplary formulation providing a preferred dosage of each ingredient to provide the body with multiple health benefits. Dosage amounts in Table 5 may be provided in a solid dosage form of one or more units, such as one or two tablets, capsules, or the equivalent in dispersible powder/granules, or about 30 ml to about 500 ml of liquid dosage forms, such as a solution or suspension. For instance, the formula disclosed in Table 5 added to about 1-16.9 ounces of cold water generates a composition similar to the composition of typical chicken soup. The formula may alternatively be designed as a dissolving tablet, capsule, suspension, or solution.

TABLE 5

| Ingredient | Individual Dose/Twice Daily Dose of the Invention |
| --- | --- |
| Beta Carotene | 8076 IU/1,652 IU |
| Alpha Carotene | 473 mcg/946 mcg |
| N-acetyl cysteine | 600 mg/1200 mg |
| Lutein | 53 mcg/106 mcg |
| Zeaxanthin | 6.5 mcg/13 mcg |
| Zinc | 668 mcg/1336 mcg |
| Magnesium | 28 mg/56 mg |
| Thiamine | 900 mcg/1800 mcg |
| Calcium | 28 mg/56 mg |
| Vitamin C | 500-1000 mg/1000-2000 mg |

As explained previously, it should be understood that the four aforementioned exemplary formulations are non-limiting, and it should be appreciated that the various ingredients described herein may be used in any combination, provided that the composition includes NAC and either vitamin A, vitamin C or at least one carotenoid.

Example 6

Table 6 illustrates five exemplary formulations providing exemplary concentrations of additional ingredients in an examplery final adult and pediatric (ped) dosage forms. The formulations summarized in the table may be formulated as powders, sachets, tablets etc.

TABLE 6

| Ingredient (wt %) | Powder Ped | Sachet Ped | Powder Adult | Sachet Adult | Chewable Tablet Ped |
| --- | --- | --- | --- | --- | --- |
| Dextrose | 49.80 | 52.40 | 36.97 | 39.85 | 77.30 |
| Proprietary NAC blend | 16.61 | 13.12 | 15.82 | 12.65 | 8.10 |
| Ascorbic Acid | 8.53 | 6.74 | 25.56 | 21.78 | 4.16 |
| Sucralose | 1.67 | 1.76 | 1.22 | 1.33 | 0.78 |
| Citric Acid | 6.08 | 4.79 | 3.33 | 3.63 | 0.92 |
| Malic Acid | 2.28 | 2.40 | 1.11 | 1.21 | 1.66 |
| Bitterness Suppressor | 0.91 | 0.96 | 0.89 | 0.73 | 0.71 |
| Ethyl maltol | 0.14 | 0.10 | 0.10 | 0.07 | 0.09 |
| Amino acid masker | 1.06 | 0.96 | 1.11 | 0.60 | 0.71 |
| Salt | 1.52 | | 1.00 | | |
| Vegetable Fibers | | | | | 0.83 |
| Magnesium Stearate | | | | | 1.18 |
| Sodium Bicarbonate | | 4.79 | | 4.84 | 0.50 |
| Fruit punch flavor | 9.12 | 9.59 | | | 2.37 |
| Cherry flavor | 2.28 | 2.40 | | | 0.69 |
| Creamy vanilla flavor | | | 0.89 | 1.21 | |
| Orange flavor | | | 7.78 | 8.47 | |
| Mango flavor | | | 1.67 | 1.21 | |
| Tangerine flavor | | | 2.56 | 2.42 | |

The exemplary formulas identified herein may take the form of a solid dosage form, such as a compressed and/or chewable tablet, or may be encapsulated by a water-soluble capsule for oral consumption. Alternatively, the exemplary formula may take the form of a mixable powder for mixing with a consumable liquid, or a liquid dosage form such as a solution, syrup, emulsion or a suspension. Other dosage forms, such as beads, strips, fibers, flakes or films may be used as understood by those skilled in the art. Any number and type of pharmaceutically acceptable excipients and/or carriers, such as binders, coatings, disintegrants, fillers or diluents, antiadherents, glidants, lubricants, sorbents, sweeteners, flavors, colors, suspending agents, or other preservatives may be added as understood by those skilled in the art to improve delivery and consumption of a tablet or other dosage form, for example. The exemplary formulas may be contained in a single dose (such as a single tablet) or in multiple doses, provided such multiple dosages do not exceed unsafe recommended daily allowances for any particular ingredient.

In some embodiments of the present invention, the pharmaceutically acceptable excipients in the formulation may comprise flavoring or effervescence agents selected from the group consisting of citric acid anhydrous powder, sodium bicarbonate, sodium citrate powder, sucralose, maldodextrin clintose, malic acid, orange flavor powder 151096, color yellow D &C Yellow 10, and combinations thereof. Other embodiments of the invention may be made without flavoring so it may be added to a drink such as a fruit juice. In some embodiments, the formulation may be in a form of an unflavored powder which may be added to a canned soup to provide the ingredients found in a homemade chicken soup that may be lost during the processing of canned soups. The unflavored powder may be stored in individual packets. In some embodiments, the composition may be used with bottle caps that are designed to hold dry powder, such as a KarmaCap® or PowerCap® delivery device.

According to an embodiment of the present invention, such a dose can be 1 or 2 capsules each weighing no more than 1 gram. The capsule size can be, e.g., size 00 which can be readily swallowed by a subject. Alternatively, any capsule size of up to size 000 may be used. According to an aspect of the present invention, no more than two units of the dosage form would be required to deliver any one of the aforementioned compositions. In the case of liquid dosage forms, there is no limit to the amount that can be readily swallowed. However, the total amount per dose may preferably be less than 30 ml, or approximately two table spoons.

In certain embodiments, the present invention may be used in the forms described herein as an additive to combine with other food or beverage products to fortify the product with the various formulations prior to consumption. For example, the various formulations can be added to a serving of chicken soup to increase the preexisting beneficial effects generally attributable to chicken soup. In another example, the formulation may be dispersed in a serving of tomato juice. It should be appreciated that the various formulations of the present invention may be added to any sort of consumable product at any point in the manufacturing process of the consumable product, or it may be added after manufacture but prior to consumption, where the formulation is provided in a form suitably dispersible within the targeted consumable product.

The present invention may provide for the beneficial effects generally attributed to consuming chicken soup, without spending the time needed to make chicken soup, or dehydrate or condense chicken soup. The present invention provides exceptional quality and purity of ingredients in a single dosage form not seen in dehydrated, reduced or condensed chicken soup compositions. For example, because the various ingredients as described herein can be synthesized, manufactured, or otherwise provided in a purified form, the present invention can include the effective amounts of each ingredient responsible for the various benefits of chicken soup without an excess of any particular component or the inclusion of undesired components as may be found in dehydrated or reduced products. For example, the present invention may not include any appreciable amount of sodium chloride, which is a salt that can have a negative effect on hypertension. Other ingredients that are high in caloric contents, such as fats, proteins, and carbohydrates that are found in chicken soup and which do not contribute to the therapeutic effects of chicken soup may also be absent in any appreciable amount. Embodiments of the inventive composition do not have organoleptic properties of taste, smell and/or mouth-feel of chicken soup. For the same reasons, the present invention allows for a smaller physical size of the dosage form than other related nutraceutical compositions, and thus eliminates the need to take high numbers of individual pills to achieve the effective dosages of the compositions.

For preparing pharmaceutical compositions from the compounds described by this invention, inert, pharmaceutically acceptable diluents, excipients and carriers can be either solid or liquid. Solid form preparations include powders, tablets, dispersible granules, capsules (either solid-filled, semi-solid filled or liquid-filled), sachets and suppositories. The powders and tablets may be comprised of from about 5 to about 95 percent active ingredient. Suitable solid carriers can be, e.g., magnesium carbonate, magnesium stearate, talc, sugar or lactose. Tablets, powders, sachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18$^{th}$ Edition, (1990), Mack Publishing Co., Easton, Pa. which is incorporated by reference. Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants that may be mentioned for use in these dosage forms are, metallic stearates, talc, starch powder, stearic acid, different grades of polyethylene-glycol and the like. Disintegrants include starch, methylcellulose, guar gum and the like. Sweetening and flavoring agents and preservatives may also be included where appropriate.

Additionally, the compositions of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injection or addition of sweeteners and pacifiers for oral solutions, suspensions and emulsions. Liquid form preparations may also include solutions for intranasal administration.

Those of ordinary skill in the art will recognize that many modifications and variations of the present invention may be implemented without departing from the spirit or scope of the invention. Thus, it is intended that the present invention cover the modification and variations of this invention provided they come within the scope of the appended claims and their equivalents.

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

Reference throughout this specification to numerical ranges should not be construed as limiting and should be understood as encompassing the outer limits of the range as well as each number and/or narrower range within the enumerated numerical range.

The term "about", when referring to a physical quantity, is to be understood to include measurement errors within, and inclusive of 10%. For example, "about 100° C." should be understood to mean "100±10° C."

What is claimed is:

1. A composition for improving the health of a subject comprising:
    about 250-1500 mg of n-acetyl cysteine;
    about 1-1500 mg of vitamin C; and
    a carotenoid selected from the group consisting of alpha carotene, beta carotene, lutein, zeaxanthin, and combinations thereof.

2. The composition of claim 1, wherein the composition is in a solid or in a liquid form.

3. The composition of claim 1, wherein the composition is in a form selected from the group consisting of a tablet, capsule, dispersible powder or granules, emulsion, syrup, suspension and solution.

4. The composition of claim 1, comprising about 32-32,000 mcg of alpha carotene;
    about 1-10 mg of beta carotene;
    about 4-400 mcg of lutein; and
    about 0.5-50 mcg of zeaxanthin.

5. The composition of claim 1, wherein the carotenoid comprises alpha carotene in an amount of about 32-32,000 mcg.

6. The composition of claim 1, wherein the carotenoid further comprises beta carotene in an amount of about 1-10 mg.

7. The composition of claim 1, wherein the carotenoid further comprises lutein in an amount of about 4-400 mcg.

8. The composition of claim 1, wherein the carotenoid further comprises zeaxanthin in an amount of about 0.5-50 mcg.

9. The composition of claim 1, further comprising one or more of calcium, thiamine, magnesium, manganese, phosphorous, and zinc.

10. The composition of claim 9, wherein the amount of:
    calcium is about 2-200 mg;
    thiamine is about 60-6000 mcg;
    magnesium is about 2-200 mg; and
    zinc is about 44-4,400 mcg.

11. The composition of claim 10, further comprising a bitterness suppressor, ethyl maltol, amino acid masker, salt, vegetable fibers, magnesium stearate, sodium bicarbonate, flavoring agents, and combinations thereof.

12. The composition of claim 2, wherein the composition is in a form of dispersible powder or granules with effervescent.

13. The composition of claim 9, wherein none of the n-acetyl cysteine, vitamin C, alpha carotene, beta carotene, lutein, and zeaxanthin are derived from chicken soup.

* * * * *